(12) United States Patent
Feldman et al.

(10) Patent No.: US 10,481,101 B2
(45) Date of Patent: Nov. 19, 2019

(54) ASYMMETRICAL MAGNIFICATION INSPECTION SYSTEM AND ILLUMINATION MODULE

(71) Applicant: APPLIED MATERIALS ISRAEL LTD., Rehovot (IL)

(72) Inventors: Haim Feldman, Nof-Ayalon (IL); Boris Golberg, Ashdod (IL); Ido Dolev, Rehovot (IL)

(73) Assignee: Applied Materials Israel Ltd., Rehovot (IL)

( * ) Notice: Subject to any disclaimer, the term of this patent is extended or adjusted under 35 U.S.C. 154(b) by 219 days.

(21) Appl. No.: 15/412,879

(22) Filed: Jan. 23, 2017

(65) Prior Publication Data

US 2018/0209915 A1    Jul. 26, 2018

(51) Int. Cl.
*G01N 21/88* (2006.01)
*G01N 21/95* (2006.01)
(Continued)

(52) U.S. Cl.
CPC ..... *G01N 21/8806* (2013.01); *G01N 21/8851* (2013.01); *G01N 21/9501* (2013.01); *G02B 21/0016* (2013.01); *G02B 21/06* (2013.01); *G02B 26/0891* (2013.01); *G02B 27/0911* (2013.01); *G02B 27/0972* (2013.01)

(58) Field of Classification Search
CPC ........... G01N 21/8806; G01N 21/8851; G01N 21/9501; G01N 21/956; G01N 21/94; G01N 2021/887; G01N 2021/8822; G01N 21/47; G01N 2201/06113; G01N 21/9506; G01N 21/958; G01N 29/2418; G01N 21/88; G01N 25/72; G01N 2021/4792; G01N 2021/9511; G01N 21/90; G01N 21/9045; G01N 21/954; G02B 21/0016; G02B 21/06; G02B 26/0891; G02B 27/0911; G02B 27/0972; G02B 13/08; G02B 13/10; G06T 2207/10056; G06T 2207/30148; G06T 7/0004; G06T 2207/30141; G01B 11/06; G01B 11/306; G01B 11/25; G01B 11/26; G03F 7/7065; G03F 1/84
USPC .... 348/87; 359/207.1, 226.2, 633, 637, 640, 359/668, 669, 670, 719, 737
See application file for complete search history.

(56) References Cited

U.S. PATENT DOCUMENTS

| 7,646,546 | B1* | 1/2010 | O'Shaughnessy ........................... G02B 27/0081 327/100 |
| 2007/0064240 | A1* | 3/2007 | Hill ....................... G01B 11/272 356/487 |
| 2014/0260640 | A1* | 9/2014 | Sullivan ............. G01N 29/2418 73/655 |

\* cited by examiner

*Primary Examiner* — Nathnael Aynalem
(74) *Attorney, Agent, or Firm* — Kilpatrick Townsend & Stockton LLP

(57) ABSTRACT

An illumination module that includes a pair of anamorphic prisms that comprises a first anamorphic prism and a second anamorphic prism; wherein the pair of anamorphic prisms is configured to (a) receive a first radiation beam that propagates along a first optical axis, and (b) asymmetrically magnify the first radiation beam to provide a second radiation beam that propagates along a second optical axis that is parallel to the first optical axis; and a rectangular prism that is configured to receive the second radiation beam and perform a lateral shift of the second radiation beam to provide a third radiation beam; and a rotating mechanism that is configured to change an asymmetrical magnification of the pair of anamorphic prisms by rotating at least one of the first anamorphic prism and the second anamorphic prism.

14 Claims, 7 Drawing Sheets

(51) Int. Cl.
*G02B 21/00* (2006.01)
*G02B 21/06* (2006.01)
*G02B 27/09* (2006.01)
*G02B 26/08* (2006.01)

ASYMMETRICAL MAGNIFICATION INSPECTION SYSTEM AND ILLUMINATION MODULE

BACKGROUND

There is a growing need to provide compact and adjustable inspection systems and illumination modules for inspecting objects such as semiconductor wafers.

SUMMARY

This summary merely illustrates various examples of method and/or systems and/or modules. It should not be used to limit the scope of the claims.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION

Usually it is desirable in double dark field tools to increase throughput as much as possible, but still keep sensitivity. One way for doing this is to use an elliptical illumination aperture, the spot will now be elliptical too, but the loss of sensitivity because of spot size will be compensate partially, by the increase of collection area.

Elliptical spots may be obtained by shrinking the illumination aperture in the X direction or in the Y direction.

In inspection systems, such as the Uvision tool of Applied Materials Inc. of Santa Clara Calif., the X direction is scanned by an acusto-optics device and thus has a fixed data rate, and the Y direction is scanned by moving a motorized stage.

In such a scenario the throughput can be increased by shrinking the aperture in the Y direction, and increase the stage velocity.

Figure 1:
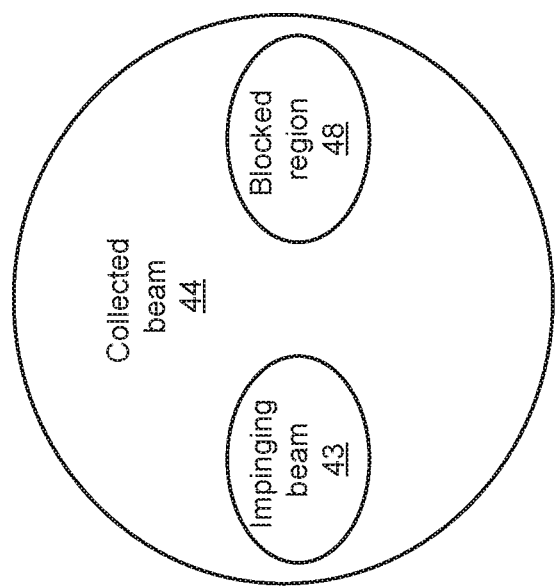
FIG. 1 illustrates an example of collection and illumination numerical apertures.
Figure 2:
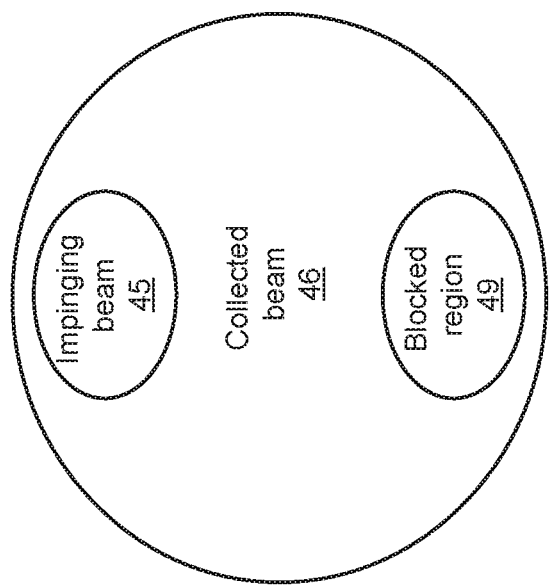
FIG. 2 illustrates an example of collection and illumination numerical apertures.

The throughput can be increased in two ways—as shown in FIGS. 1 and 2. In FIG. 1 the impinging radiation beam 43 and a blocked region 48 are at the same Y coordinates (they are "side by side"). The collected beam 44 is collected outside the blocked region 48.

In FIG. 2 the impinging radiation beam 45 and blocked region 49 are at the same X coordinates (they are "one on top the other"). The collected beam 46 is collected outside the blocked region 49.

The configuration of FIG. 2 may be better since it allows larger off-axis illumination angles which increase sensitivity in particles detections.

There may be a need to control the shape of the impinging radiation beam by changing the width-to-length ratio of the impinging radiation beam. The change may occur, for example, during the setup of inspection system, when changing the overall magnification the collection path of the inspection system, when changing a magnification of illumination path of the inspection system, or when replacing one telescope by another.

The shape of the impinging radiation beam may be determined by using an illumination module that has an adjustable asymmetrical magnification. The asymmetrical magnification of the illumination module is a ratio between (a) a width-to-length ratio of the radiation beam that exits the illumination module and (b) a width-to-length ratio of the radiation beam that enters the illumination module.

There is provided an illumination module that may include a pair of anamorphic prisms pair, a parallel plate (rectangular prism) and rotating elements for rotating the anamorphic prisms in order to adjust the asymmetrical magnification of the radiation beam.

The pair of anamorphic prisms pair and the parallel plate may be positioned upstream of any telescope of the turret—thereby an existing telescope is not replaced and the asymmetrical magnification can be easily changed over time.

The illumination module may be modular in the sense that the inspection system may operate with the illumination module or without the illumination module.

Figure 3:
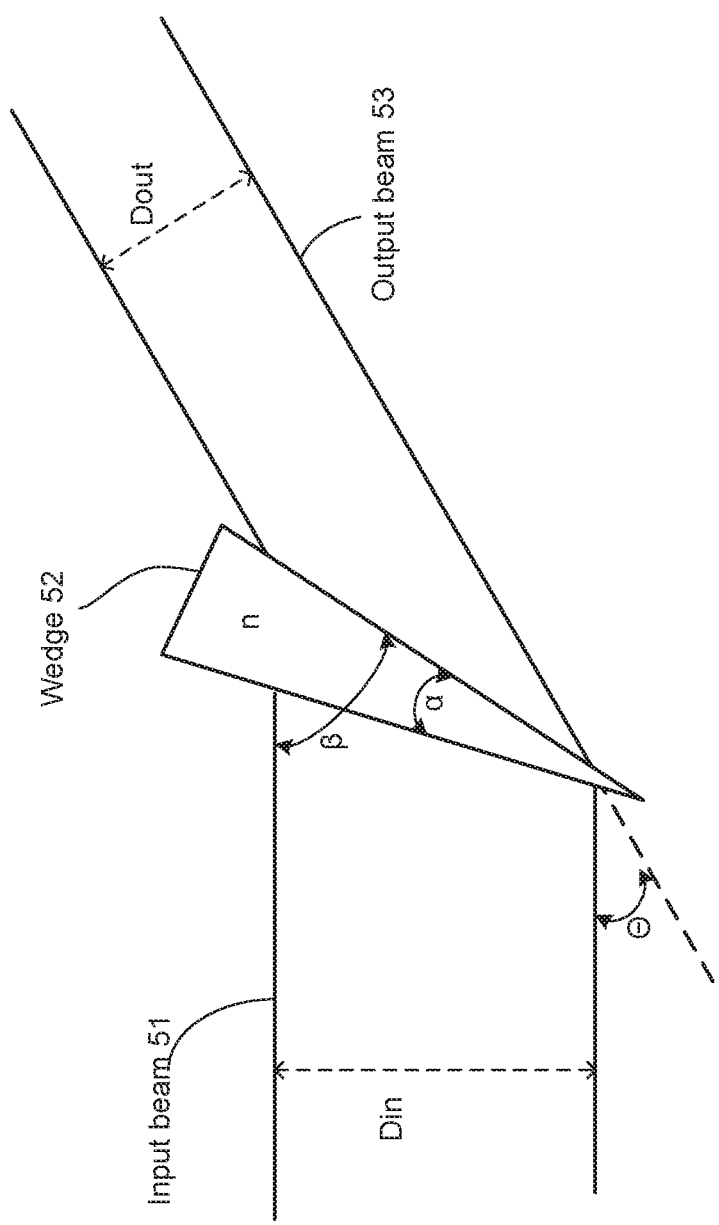
FIG. 3 illustrates an example of a wedge, an input radiation beam and an output radiation beam.

Referring to FIG. 3—when an input radiation beam 51 passes through a wedge 52 it will be tilted to provide an output radiation beam 53. The tilt is by an angle $\theta$ that substantially equals $(n-1)*\alpha$, where n is the refraction index of the wedge material and $\alpha$ is the angle between the wedge surfaces.

The output radiation beam 53 has a width (Dout) in one dimension that is smaller than the width (Din) of the input radiation beam 51 according to the break angle relative to the beam: $Dout = Din * \sinus(\beta - \theta)/\sin \beta$.

The change in the width of the beam does not affect the length of the beam. The length of the beam is measured in a plane that is normal to the plane of FIG. 3. By introducing the asymmetrical magnification, the illumination module may convert a circular radiation beam to an elliptical radiation beam.

Figure 4:
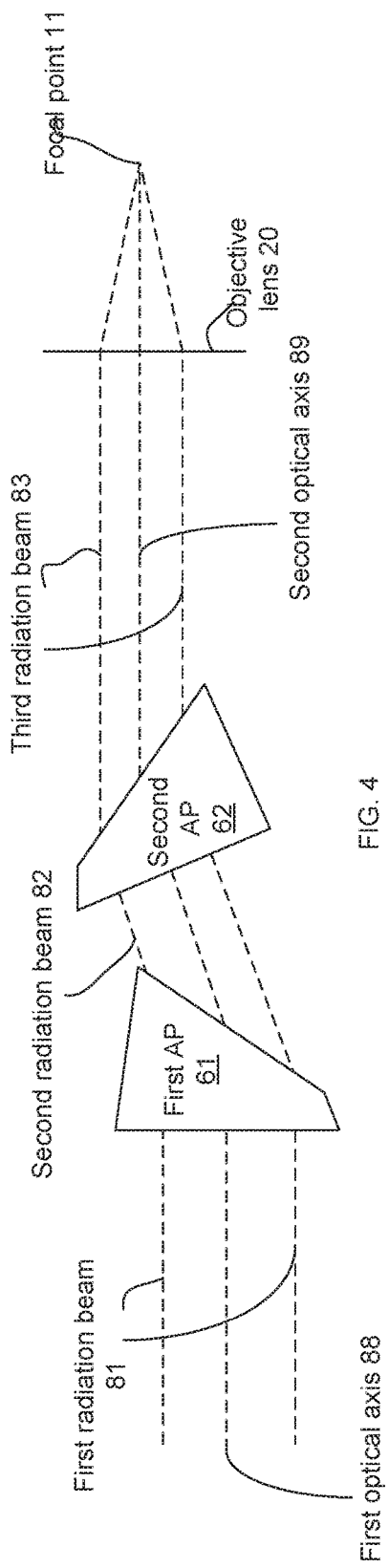
FIG. 4 illustrates an example of portion of an illumination module.

FIG. 4 illustrates a portion of an illumination module. The portion includes first anamorphic prism 61 and second anamorphic prism 62.

In FIG. 4 the first anamorphic prism 61 is denoted first AP 61 and the second anamorphic prism 62 is denoted second AP 62.

FIG. 4 also illustrates objective lens 20 and a focal point 11 of the objective lens 20. The focal point 11 may "fall" on an inspected object.

The first anamorphic prism 61 receives first radiation beam 81 (that propagates along a first optical axis 88) and outputs second radiation beam 82 towards second anamorphic prism 62. Second anamorphic prism 62 outputs the third radiation beam 83 that propagates along a second optical axis 89 that is parallel to the first optical axis.

The third radiation beam 83 is narrower (at the plane of FIG. 4) than first radiation beam 81 but has the same length (within a plane that is normal to the plane of FIG. 4) as the first radiation beam 81.

The asymmetrical magnification value may be the width-to-length ratio of the third radiation beam divided by the width-to-length ratio of the first radiation beam.

Figure 5:
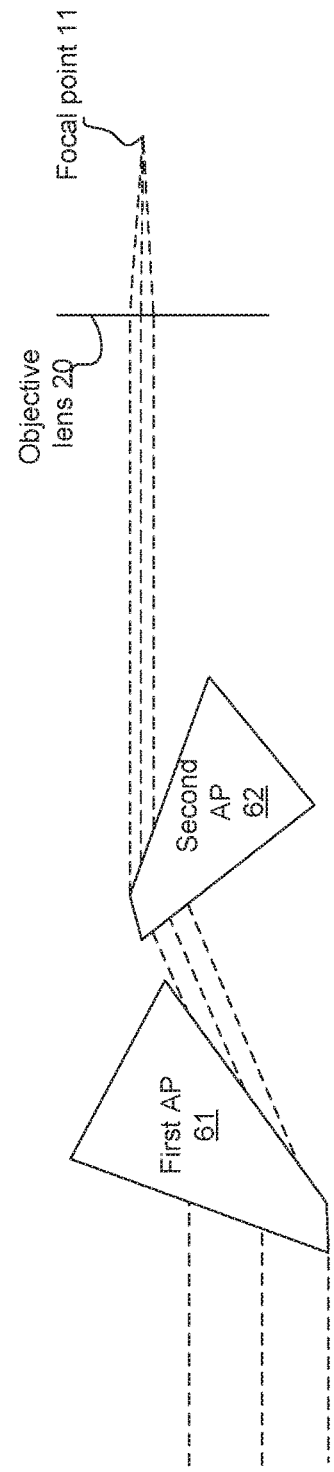
FIG. 5 illustrates an example of portion of an illumination module.

FIG. 5 illustrates a portion of an illumination module. In FIG. 5 the first anamorphic prism 61 was rotated clockwise (in relation to FIG. 4) thereby resulting in a change in the asymmetric magnification—and outputting a narrower third radiation beam (in comparison to FIG. 4).

The asymmetrical magnification may also be affected by the material of the first anamorphic prism and by the material of the second anamorphic prism.

Figure 6:
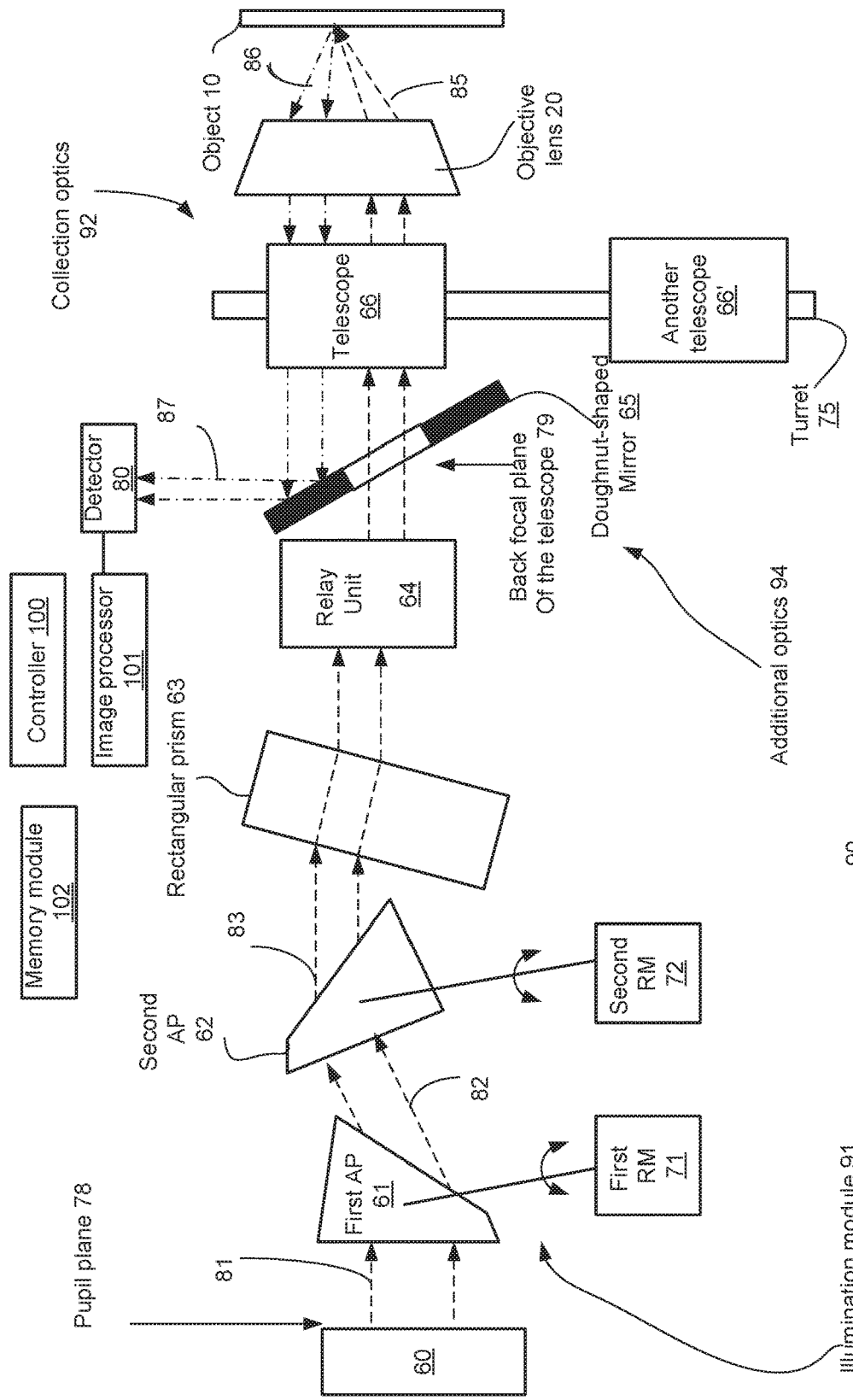
FIG. 6 illustrates an example of an inspection system.

FIG. 6 illustrates object 10 and an inspection system 90 that includes illumination module 91, collection optics 92, detector 80, image processor 101, controller 100 and memory module 102.

The illumination module 91 may include (i) a pair of anamorphic prisms that includes first anamorphic prism 61 and second anamorphic prism 62, (ii) a rotating mechanism such as first rotating unit (RM) 71 and second rotating unit (RM) 72, (iii) rectangular prism 63, (iv) relay unit 64, (v) beam splitting unit such as doughnut-shaped mirror 65, (vi) one or more telescopes such as telescope 66 and another telescope 66', and (vii) objective lens 20.

FIG. 6 also illustrates turret 75 that is connected to multiple telescopes and may be moved in order to replace one telescope by another.

The objective lens and the beam splitting unit also belong to collection optics 92.

The pair of anamorphic prisms is configured to (a) receive a first radiation beam that propagates along a first optical axis, and (b) asymmetrically magnify the first radiation beam to provide a second radiation beam that propagates along a second optical axis that is parallel to the first optical axis.

Rectangular prism 63 is configured to receive the second radiation beam and perform a lateral shift of the second radiation beam to provide a third radiation beam.

The rotating mechanism is configured to rotate at least one of the first anamorphic prism and the second anamorphic prism thereby changing an asymmetric magnification of the first radiation beam.

The relay unit 64, doughnut-shaped mirror 65, telescope 66 and objective lens 20 (collectively referred to as additional optics 94) may optically manipulate the third radiation beam 83 to provide an impinging radiation beam 85 that impinges onto object 10. The additional optics may include other or fewer optical components.

Collection optics 92 is configured to receive reflected radiation beam 86 and to pass it through the collection optics 92 to provide detected radiation beam 87 that is detected by detector 80. Collection optics 92 may include objective lens 20, telescope 66 and doughnut-shaped mirror 65. Collection optics 92 may include other or fewer optical components.

Reflected radiation beam 86 is reflected from the object 10 as a result of the illuminating of the object with the impinging radiation beam 85.

Scanner 60 is configured to scan the first radiation beam within a plane that differ from the plane of FIG. 6. For example—the first radiation beam may be scanned within a plane that is normal to the plane of FIG. 6.

The illumination module is configured to translate a scanning of the first radiation beam in pupil plane 78 to a scanning of the impinging radiation beam 85. The scanning in the pupil plane 78 is relayed to a scanning in the back focal plane 79 of the telescope.

Image processor 101 is configured to process images of the object 10. The images are constructed from detection signals generated by the detector.

Memory module 102 may be used to store images of the object 10, inspection recipes and the like.

Controller 100 is configured to control the operation of inspection system 90.

Figure 7:
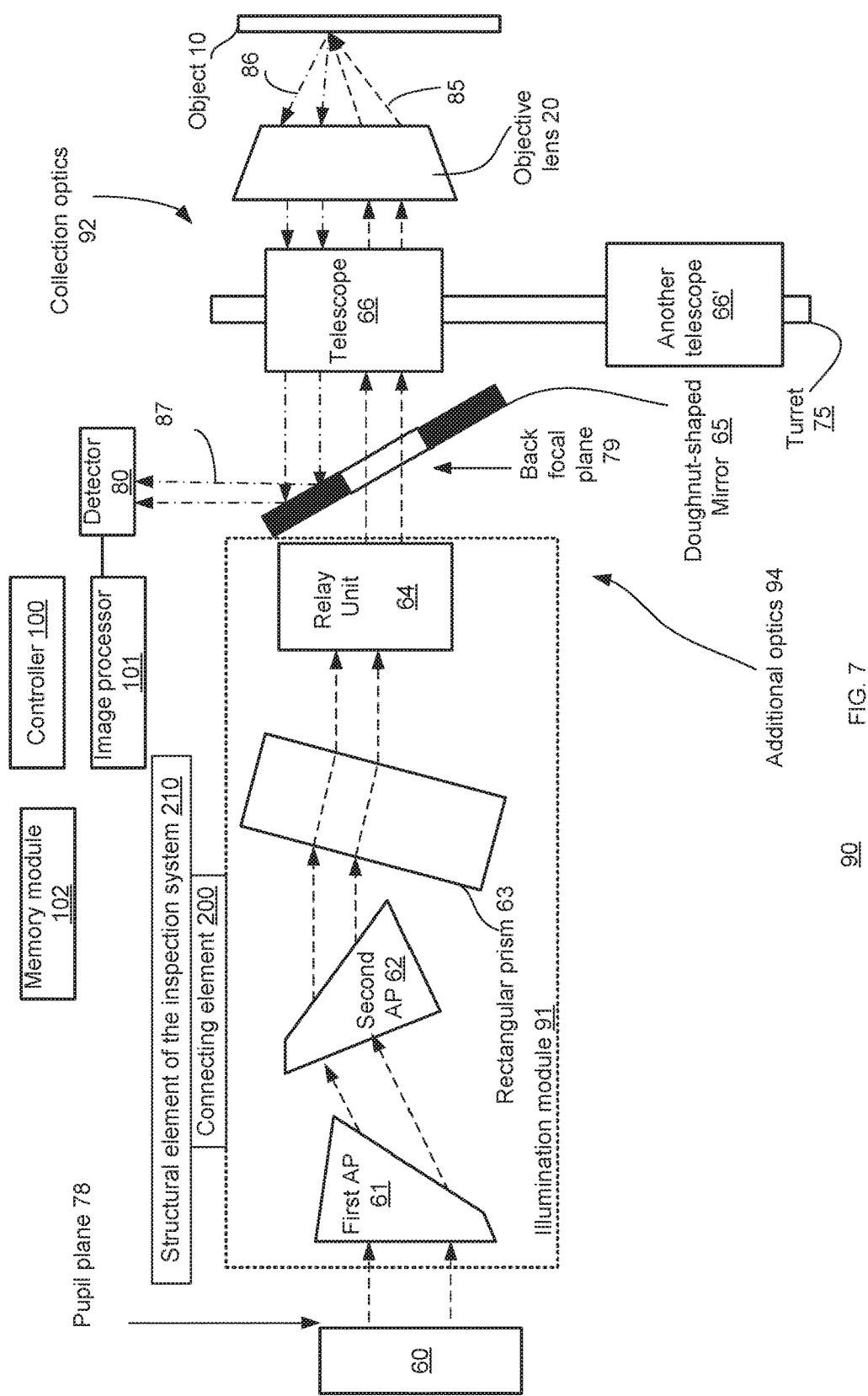
FIG. 7 illustrates an example of an inspection system.

FIG. 7 illustrates object 10 and an inspection system 90.

The inspection system of FIG. 7 differs from the inspection system of FIG. 6 by:
a. Not including the first rotating unit 71.
b. Not including the second rotating unit 72.
c. Illustrating a connecting element 200 that connects between the illumination module 91 and a structural element 210 of the inspection system.

The connecting element 200 enables to connect the illumination module to the structural element 210 and allows to disconnect the illumination module to the structural element. The structural element may be a sidewall, a rod, a housing, a cage, and the like.

The inspection system 90 may operate with or without the illumination module 91. The illumination module is, in a sense, a modular module that can be added or removed depending upon the object inspected, the inspection recipe, and the like.

Any of the previously illustrated illumination modules can be also regarded as modular modules.

Figure 8:
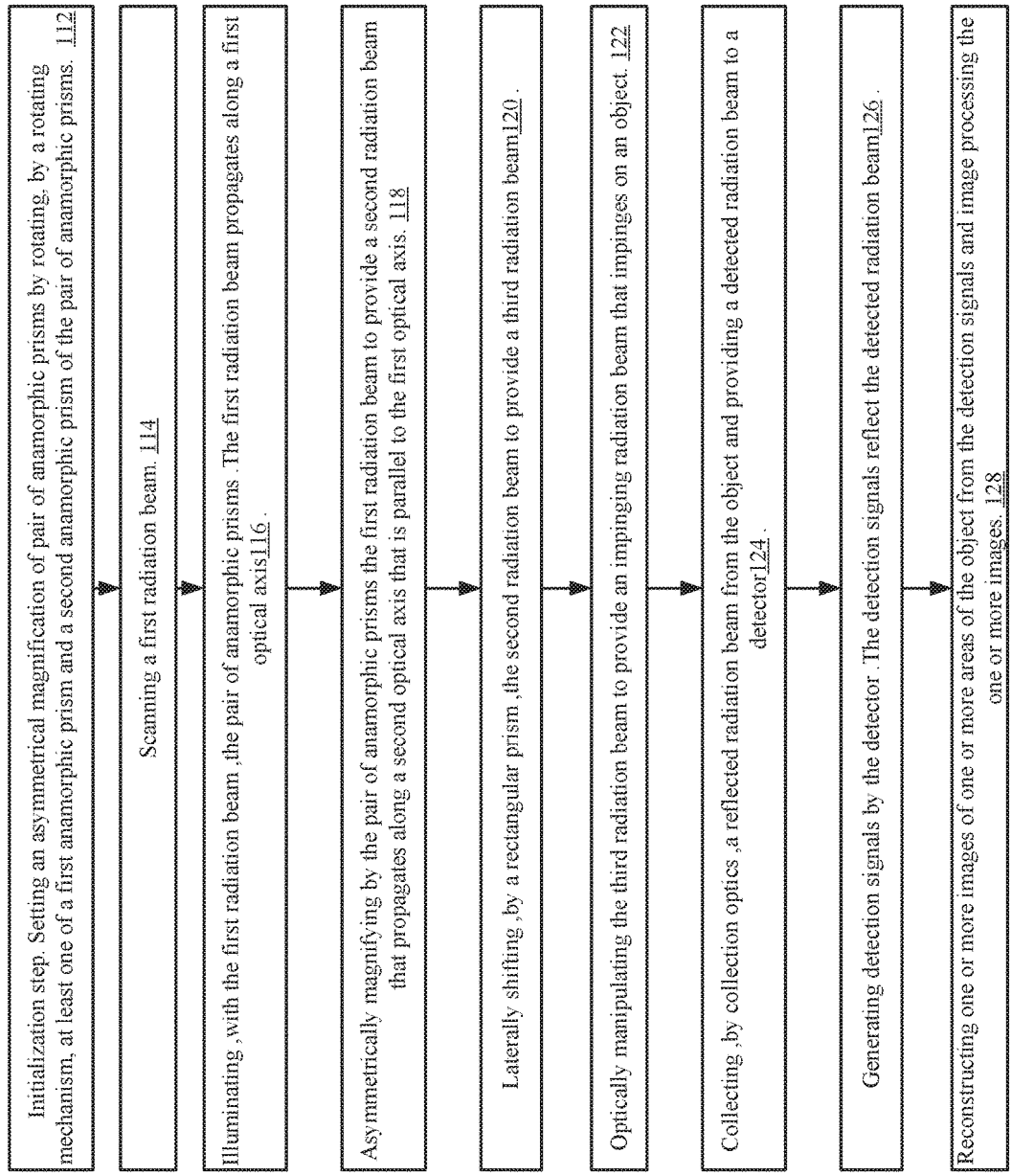
FIG. 8 illustrates an example of a method.

FIG. 8 illustrates an example of a method 110.

Method 110 may start by initialization step 112.

Initialization step 112 may include setting an asymmetrical magnification of pair of anamorphic prisms by rotating, by a rotating mechanism, at least one of a first anamorphic prism and a second anamorphic prism of the pair of anamorphic prisms. If the pair is already set to provide a desired asymmetrical magnification, then there is no need to rotate either one of the first and second anamorphic prisms.

Initialization step 112 may be followed by step 114 of scanning a first radiation beam.

Step 114 may be followed by step 116 of illuminating, with the first radiation beam, the pair of anamorphic prisms. The first radiation beam propagates along a first optical axis.

Step 116 may be followed by step 118 of asymmetrically magnifying, by the pair of anamorphic prisms, the first radiation beam to provide a second radiation beam that propagates along a second optical axis that is parallel to the first optical axis.

Step 118 may be followed by step 120 of laterally shifting, by a rectangular prism, the second radiation beam to provide a third radiation beam.

Step 120 may be followed by step 122 of optically manipulating the third radiation beam to provide an impinging radiation beam that impinges on an object.

Step 122 may be followed by step 124 of collecting, by collection optics, a reflected radiation beam from the object and providing a detected radiation beam to a detector.

Step 124 may be followed by step 126 of generating detection signals by the detector. The detection signals reflect the detected radiation beam.

Step 126 may be followed by step 128 of reconstructing one or more images of one or more areas of the object from the detection signals and image processing the one or more images.

The image processing may be executed during a defect detection process, during a review process and/or during a metrology process.

The object may be a semiconductor wafer, a lithographic mask, a solar panel or any object that includes microscopic and even nano-metric structural elements.

The radiation may be visible light, ultra-violet, extreme ultra-violet, deep ultra-violet, near infrared, and the like.

While a number of exemplary aspects and embodiments have been discussed above, those of skill in the art will recognize certain modifications, permutations, additions and sub combinations thereof. It is therefore intended that the following appended claims and claims hereafter introduced be interpreted to include all such modifications, permutations, additions and sub-combinations as are within their true spirit and scope.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description. While preferred embodiments of the present invention have been shown and described, it should be understood that various alternatives, substitutions, and equivalents can be used, and the present invention should only be limited by the claims and equivalents thereof.

What is claimed is:

1. An illumination module, comprising:
a pair of anamorphic prisms that comprises a first anamorphic prism and a second anamorphic prism; wherein the pair of anamorphic prisms is configured to (a) receive a first radiation beam that propagates along a first optical axis, and (b) asymmetrically magnify the first radiation beam to provide a second radiation beam that propagates along a second optical axis that is parallel to the first optical axis;
a rectangular prism that is configured to receive the second radiation beam and perform a lateral shift of the second radiation beam to provide a third radiation beam, wherein the pair of anamorphic prisms is configured to introduce a lateral shift between the first radiation beam and the second radiation beam, and wherein the lateral shift introduced by the rectangular prism is configured to compensate for the lateral shift introduced by the anamorphic prisms; and
a rotating mechanism that is configured to change an asymmetrical magnification of the pair of anamorphic prisms by rotating at least one of the first anamorphic prism and the second anamorphic prism.

2. The illumination module according to claim 1 wherein the rotating mechanism comprises a first rotating unit for rotating the first anamorphic prism and a second rotating unit for rotating the second anamorphic prism.

3. The illumination module according to claim 1, comprising a relay lens, beam splitting optics, a telescope and an objective lens.

4. The illumination module according to claim 3, comprising a scanner for scanning the first radiation beam; and wherein the illumination module is configured to relay a scanning of the first radiation beam at a pupil plane to a scan on a back focal plane of the telescope.

5. An inspection system that comprises
a detector;
collection optics;
an illumination module that is detachably connected to a structural element of the inspection system;
multiple telescopes that are held by a turret and are positioned between the illumination module and an object;
wherein the illumination module comprises:
a pair of anamorphic prisms that comprises a first anamorphic prism and a second anamorphic prism; wherein the pair of anamorphic prisms is configured to (a) receive a first radiation beam that propagates along a first optical axis, and (b) asymmetrically magnify the first radiation beam to provide a second radiation beam that propagates along a second optical axis that is parallel to the first optical axis;
a rectangular prism that is configured to receive the second radiation beam and perform a lateral shift of the second radiation beam to provide a third radiation beam; and
additional optics for optically manipulating the third radiation beam to provide an impinging radiation beam that impinges onto the object; and
wherein the collection optics is configured to direct a reflected radiation beam towards the detector; wherein the reflected radiation beam is reflected from the object as a result of illuminating of the object with the impinging radiation beam.

6. The inspection system according to claim 5, wherein the illumination module comprises a rotating mechanism that is configured to rotate at least one of the first anamorphic prism and the second anamorphic prism thereby changing an asymmetrical magnification of the pair of anamorphic prisms.

7. The inspection system according to claim 6, wherein the rotating mechanism comprises a first rotating unit for rotating the first anamorphic prism and a second rotating unit for rotating the second anamorphic prism.

8. The inspection system according to claim 5, comprising a scanner for scanning the first radiation beam; and wherein the illumination module is configured to translate a scanning of the first radiation beam to a scanning of the impinging radiation beam.

9. The inspection system according to claim 5, comprising an image processor that is configured to process images of the object; and wherein the images are constructed from detection signals generated by the detector.

10. The inspection system according to claim 5, wherein the pair of anamorphic prisms is configured to introduce a certain lateral shift between the first radiation beam and the second radiation beam; and wherein the lateral shift introduced by the rectangular prism is configured to compensate for the certain lateral shift.

11. The inspection system according to claim 5 further comprising a scanner for scanning the first radiation beam; and wherein the illumination module is configured to relay a scanning of the first radiation beam at a pupil plane to a scan on a back focal plane of a telescope.

12. A method for illuminating an object, the method comprises:

setting an asymmetrical magnification of a pair of anamorphic prisms by rotating, by a rotating mechanism, at least one of a first anamorphic prism and a second anamorphic prism of the pair of anamorphic prisms;

illuminating, with a first radiation beam, the pair of anamorphic prisms; wherein the first radiation beam propagates along a first optical axis;

asymmetrically magnifying, by the pair of anamorphic prisms, the first radiation beam in one dimension to provide a second radiation beam that propagates along a second optical axis that is parallel to the first optical axis; and laterally shifting, by a rectangular prism, the second radiation beam to provide a third radiation beam, wherein the pair of anamorphic prisms is configured to introduce a lateral shift between the first radiation beam and the second radiation beam, and wherein the lateral shift introduced by the rectangular prism is configured to compensate for the lateral shift introduced by the pair of anamorphic prisms.

13. The method according to claim 12 wherein the third radiation beam propagates along the first optical axis.

14. The method according to claim 12 further comprising scanning the first radiation beam by a scanner.

* * * * *